United States Patent
Karakatsani et al.

(10) Patent No.: US 9,629,805 B2
(45) Date of Patent: Apr. 25, 2017

(54) STABILIZATION OF MOISTURE-SENSITIVE DRUGS

(71) Applicant: Amneal Pharmaceuticals LLC, Bridgewater, NJ (US)

(72) Inventors: Marianthi Karakatsani, West Chester, OH (US); Anita Kumar, Brookhaven, NY (US); Devjibhai D. Kumbhani, Brookhaven, NY (US); Pallapalayam M. Thangamathesvaran, Piscataway, NJ (US)

(73) Assignee: Amneal Pharmaceuticals LLC, Bridgewater, NJ (US)

( * ) Notice: Subject to any disclaimer, the term of this patent is extended or adjusted under 35 U.S.C. 154(b) by 0 days.

(21) Appl. No.: 14/772,999

(22) PCT Filed: Mar. 7, 2014

(86) PCT No.: PCT/US2014/021824
§ 371 (c)(1),
(2) Date: Sep. 4, 2015

(87) PCT Pub. No.: WO2014/138603
PCT Pub. Date: Sep. 12, 2014

(65) Prior Publication Data
US 2016/0030347 A1   Feb. 4, 2016

Related U.S. Application Data

(60) Provisional application No. 61/774,150, filed on Mar. 7, 2013.

(51) Int. Cl.
| | | |
|---|---|---|
| *A61K 31/195* | (2006.01) | |
| *A61K 9/16* | (2006.01) | |
| *A61K 9/20* | (2006.01) | |
| *A61K 9/28* | (2006.01) | |
| *A61K 31/222* | (2006.01) | |

(52) U.S. Cl.
CPC .......... *A61K 9/1623* (2013.01); *A61K 9/2018* (2013.01); *A61K 9/2095* (2013.01); *A61K 9/284* (2013.01); *A61K 9/2893* (2013.01); *A61K 31/222* (2013.01)

(58) Field of Classification Search
CPC .. A61K 9/1623; A61K 9/2018; A61K 9/2095; A61K 9/2893; A61K 31/222
USPC .................................................. 514/564
See application file for complete search history.

(56) References Cited

U.S. PATENT DOCUMENTS

| | | | |
|---|---|---|---|
| 6,039,813 A | 3/2000 | Pepper et al. | |
| 7,807,715 B2 | 10/2010 | Arth et al. | |
| 2007/0122476 A1 | 5/2007 | Hanshew, Jr. et al. | |
| 2008/0138421 A1* | 6/2008 | Arth .................. | A61K 47/10 424/489 |
| 2008/0318982 A1* | 12/2008 | Mastrell .............. | A61K 31/025 514/262.1 |
| 2009/0252805 A1* | 10/2009 | Piene .................. | A23L 1/097 424/490 |
| 2011/0123692 A1 | 5/2011 | Eroma et al. | |

FOREIGN PATENT DOCUMENTS

| | | |
|---|---|---|
| EP | 2177213 A1 | 4/2010 |
| EP | 2508173 | 10/2012 |
| WO | 2005/117829 A2 | 12/2005 |
| WO | WO-2008/062435 | 5/2008 |
| WO | WO-2012/098499 | 7/2012 |

OTHER PUBLICATIONS

Rowe et al, Handbook of Pharmaceutical Excipients, 6th ed., 2009, p. 1 and 414-415.*
PCT International Preliminary Report on Patentability in PCT/US2014/021824, dated Sep. 8, 2015, 8 pages.
PCT International Search Report and Written Opinion in PCT/US2014/021824, mailed Jun. 24, 2014, 13 pages.
Reddy, B.V. Rami, et al., A Validated Stability-Indicating HPLC Assay Method for Determination of Fesoterodine Fumarate, *RASAYAN J. Chem.* vol. 5 No. 2 Apr.-Jun. 2012, 239-245.

* cited by examiner

*Primary Examiner* — T. Victor Oh
(74) *Attorney, Agent, or Firm* — Servilla Whitney LLC

(57) ABSTRACT

Described are stability-enhancing formulations of drugs that are sensitive to moisture. The formulations comprise co-granulates containing a moisture-sensitive drug and an excipient selected from fructose, xylitol, maltitol, and mixtures thereof. Also described are methods of producing a pharmaceutical tablet. The method comprises forming a blend of a moisture-sensitive drug and a first excipient selected from fructose, xylitol, maltitol, and mixtures thereof; spraying the blend with water to produce granules; drying and milling the granules; mixing a second excipient with the granules; and compressing into tablets.

11 Claims, No Drawings

STABILIZATION OF MOISTURE-SENSITIVE DRUGS

CROSS-REFERENCE TO RELATED APPLICATIONS

This application is the National Stage Entry of PCT/US2014/021824, filed Mar. 7, 2014, which claims priority to U.S. Provisional Application Ser. No. 61/774,150, filed on Mar. 7, 2013, the contents of which are incorporated herein by reference in their entireties.

TECHNICAL FIELD

The present disclosure relates generally to stability-enhancing formulations of drugs that are sensitive to moisture.

BACKGROUND

There are many drug substances that exhibit undesirable changes when exposed to a moist environment, prior to administration. Depending on the particular drug, the changes can result from internal molecular changes such as hydrolysis, or from reactions with other components of the drug product formulation or with the atmosphere. Since drug product manufacturing cannot always be conducted in an environment having a low humidity, there can be significant drug degradation during the various production operations, prior to packaging a product. After packaging, stability of the products can be affected by moisture transfer through packaging components, as well as reactions involving components of the package atmosphere. Also, repeatedly opening and closing a package during normal use can expose the contents to atmospheric moisture. Due to normal fluctuations in the moisture content of the atmosphere, undesired changes that will be experienced with a moisture-sensitive drug are not predictable.

A frequent result of contact between a sensitive drug compound and moisture is a reaction that results in formation of one or more different chemical species. This can be simply a hydration of the drug molecule that results in different dissolution or other physical properties, or it can involve a reaction that produces a different compound having a diminished intended pharmacological activity. In some instances, a new molecular entity that is produced can have a radically different pharmacological activity that is harmful when administered.

Regulatory agencies require demonstration of drug stability, before marketing approval can be given. This requirement includes maintenance of at least a minimum drug content during the expected shelf-life of the formulated product, while the unopened package is stored in a specified temperature and humidity environment. Where the drug is particularly sensitive to moisture, sometimes the packaging will incorporate a desiccant component to absorb moisture entering through the packaging materials and/or during repeated brief openings of the package.

There have been some approaches developed for reducing the effects of moisture on sensitive drugs. Sometimes the drug substance can be combined with a protective hydrophobic material, such as an oil or polymer. However, this frequently leads to other undesired effects, such as altering the drug solubility parameters, and can create difficulties in processing to manufacture a formulated product.

According to U.S. Pat. No. 7,807,715 it is necessary to enhance the chemical stability of fesoterodine and its salts in formulations, and this can be accomplished by granulating a mixture of the drug and a stabilizer selected from the group consisting of sorbitol, xylitol, polydextrose, isomalt, dextrose, and combinations thereof. The granulate is combined with excipient materials and compressed into tablet products. This patent, in its examples, teaches that mannitol, maltitol, and lactose act to increase the degradation of fesoterodine hydrogen fumarate, during storage of their granulates under various temperature and humidity conditions, so would not be desirable in granulation mixtures.

The drug fesoterodine fumarate is the active ingredient in a product being sold as TOVIAZ® tablets to treat urinary incontinence and frequency problems. Inactive ingredients are glyceryl behenate, hypromellose, indigo carmine aluminum lake, lactose monohydrate, soya lecithin, microcrystalline cellulose, polyethylene glycol, polyvinyl alcohol, talc, titanium dioxide, and xylitol. The xylitol apparently is used as a drug stabilizer in the TOVIAZ product.

International Patent Application Publication No. WO 2012/098499 describes stabilizing fesoterodine fumarate by forming a molecular dispersion of the drug with an alkyl hydroxyalkylcellulose ether, a hydroxyalkylcellulose ether, an ester of either, or a mixture of any two or more thereof. The dispersion is said to not contain the drug in its crystalline or amorphous form, but has suitable stability.

European Patent Application Publication No. 2 508 173 describes stabilizing fesoterodine, or a salt or solvate thereof, by granulating with sucrose, polyethylene glycol, cyclodextrin, maltodextrin, or combinations thereof.

Considering all of these teachings, it becomes apparent that predicting the stability of a drug, when it is to be combined with various excipient substances, is not possible. Considerable effort is required to find suitable combinations that will deliver a moisture-sensitive drug in a desired, reproducible manner, facilitate pharmaceutical dosage form preparation, and provide the required drug stability during manufacturing, storage, and use.

SUMMARY

A first aspect of the present invention is directed to a pharmaceutical formulation. In a first embodiments, a pharmaceutical formulation comprises a co-granulate comprising a moisture-sensitive drug and an excipient selected from the group consisting of fructose, a mixture of xylitol and maltitol, and combinations thereof.

In a second embodiment, the pharmaceutical formulation of the first embodiment is modified, wherein the excipient is fructose.

In a third embodiment, the pharmaceutical formulation of the second embodiment is modified, wherein the moisture-sensitive drug and fructose are present in a weight ratio of about 1:9.

In a fourth embodiment, the pharmaceutical formulation of the first embodiment is modified, wherein the excipient is a mixture of xylitol and maltitol.

In a fifth embodiment, the pharmaceutical formulation of the fourth embodiment is modified, wherein the moisture-sensitive drug, xylitol, and maltitol are present in a weight ratio in the range of about 1:2:2 to 1:2:7.

In a sixth embodiment, the pharmaceutical formulation of the fourth and fifth embodiments is modified, wherein the moisture-sensitive drug, xylitol, and maltitol are present in a weight ratio of about 1:2:4.

In a seventh embodiment, the pharmaceutical formulation of the first through sixth embodiments is modified, wherein the moisture-sensitive drug comprises fesoterodine fumarate.

In an eighth embodiment, the pharmaceutical formulation of the first through seventh embodiments is modified wherein the pharmaceutical formulation further comprises a diluent, a binder, a drug stabilizer, a disintegrant, a glidant, a lubricant, a release rate modifier, a preservative, an antioxidant, a coating, a colorant, a flavoring agent, or combinations thereof.

A second aspect of the present invention is directed to a method. In a ninth embodiment, a method of producing a pharmaceutical tablet comprises: forming a blend of a moisture-sensitive drug and a first excipient selected from the group consisting of fructose, a mixture of xylitol and maltitol, and combinations thereof; spraying the blend with water to produce granules; drying and milling the granules; mixing a second excipient with the granules; and compressing into tablets.

In a tenth embodiment, the method of the ninth embodiment is modified, wherein the first excipient is fructose.

In an eleventh embodiment, the method of the ninth embodiment is modified, wherein the first excipient is a mixture of xylitol and maltitol.

In a twelfth embodiment, the method of the ninth through eleventh embodiments is modified, wherein the second excipient is selected from the group consisting of diluent, binder, drug stabilizer, disintegrant, glidant, lubricant, release rate modifier, preservative, antioxidant, coating, colorant, flavoring agent, or combinations thereof.

In a thirteenth embodiment, the method of the ninth through twelfth embodiments is modified, wherein the moisture-sensitive drug comprises fesoterodine fumarate.

In a fourteenth embodiment, the method of the ninth through twelfth embodiments is modified, wherein the granules are dried and milled to an average particle size of less than 1200 μm.

In a fifteenth embodiment, the method of the ninth through twelfth embodiments is modified wherein the method further comprises coating the tablets with a coating suspension.

A third aspect of the present invention is directed to a table tablet. In a sixteenth embodiment, a tablet for oral administration comprises a co-granulate consisting of fesoterodine fumarate and fructose in a ratio of about 1:9, and one or more additional pharmaceutically acceptable excipients.

DETAILED DESCRIPTION

Numerous moisture-sensitive drugs are known, such as amlodipine, felodipine, fesoterodine, isradipine, nifedipine, nimodipine, nisoldipine, etc. Mention of any drug compound is intended to include the base drug as well as any of its salts, esters, solvates, etc. that will be useful for delivering the drug. In the following discussion, fesoterodine is used as a representative for moisture-sensitive drugs, for purposes of brevity. However, the scope of the present disclosure is not to be limited to this particular drug.

Moisture sensitivity is intended to encompass any undesired changes in a drug substance that occur as a result of exposure to moisture, such as atmospheric humidity. Such changes can involve drug compound degradation that forms one or more impurities, changes in physical characteristics, morphological changes, etc.

In some instances, drug stability is evidenced by a slow rate of degradant compound formation, over time. The period of time, during which a drug must remain stable, i.e., maintain its potency and/or impurity content in a formulation, varies according to commercial specifications set by the manufacturer. For example, a particular product might be required to maintain certain potency specifications for a period of six months, one year, two years, or some other time following manufacturing. The established shelf life of a product presumes maintenance in the original packaging, in specified temperature and humidity environments.

Fesoterodine fumarate is used to treat urinary incontinence and has the structural formula shown below. A chemical name for the drug is isobutyric acid 2-[(R)-3-diisopropylammonium-1-phenylpropyl]-4-(hydroxymethyl) phenyl ester hydrogen fumarate.

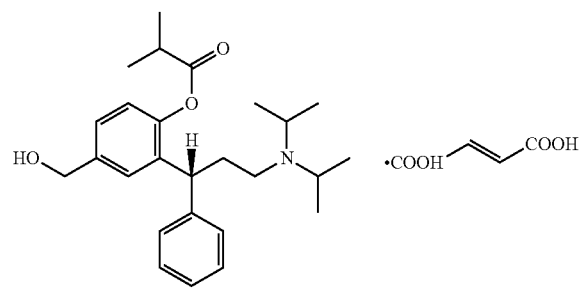

When exposed to moisture, fesoterodine tends to degrade, forming inter alia a deacylated molecule having the structural formula shown below, or a salt thereof. This degradant can be used as a marker for fesoterodine degradation.

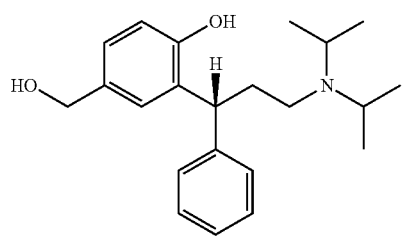 [SMILES: CC(C)N(CC[C@H](c1ccccc1)c1cc(CO)ccc1O)C(C)C]

Products containing fesoterodine can be analyzed for their fesoterodine content and the contents of the various degradant impurities, using high performance liquid chromatography (HPLC) methods.

Degradation of fesoterodine and other moisture-sensitive drugs can be inhibited by co-granulation of the drug with certain excipients, and use of the granulates to prepare the desired solid dosage forms such as tablets and capsules. Particularly useful excipients for co-granulation are fructose and mixtures of xylitol and maltitol.

Several sugars and sugar alcohols have been tested to determine their suitability for co-granulation with fesoterodine. The experiments involved wet granulating the drug with varying proportions of excipient, using small amounts of water. In the cases of xylitol and maltitol, respectively having mean particle sizes of 300 μm and 200 μm, it was found that simply mixing the drug and excipient powders formed hard agglomerated particles that would not pass easily through a 40 mesh sieve (having 0.42 mm openings), indicating that further processing the mixtures into formulated products might involve some difficulties. Several other excipients were found to not stabilize the drug, some of them even appearing to promote degradation of the drug.

It has now been determined that fructose, and mixtures of xylitol and maltitol, can advantageously be used in cogranulations with moisture-sensitive drugs to promote stability of the drugs in their pharmaceutical formulations.

Co-granulation can be conducted as a wet process or a dry process. In a wet process, a moving bed of a mixture of powdered ingredients, including a drug substance, is sprayed with a small quantity of a liquid to form granules. The liquid can be aqueous or non-aqueous, and can optionally contain one or more dissolved or dispersed excipients, such as a binder or antioxidant. In some instances, the liquid will be a neat liquid ingredient, such as water, an alcohol, a substituted or unsubstituted hydrocarbon, etc. It is not necessary that the liquid ingredient is capable of dissolving some portion of a drug or solid excipient in the powder mixture, as typically it is only required to wet the particles. However, liquids having a degree of solvent properties frequently are used. After the spraying is completed, the granules may be sized by passing through a sieve and are dried. Dry granules can further be subjected to a size reduction procedure, if desired.

Dry granulation may include passing a powder mixture through a roller compactor, then crushing and sizing the compacted material. Alternatively, a powder mixture can be compacted by a compression process called "slugging," producing large (e.g., about 25 mm) flat tablets or plates, which are then crushed and sized.

Following the granulation procedure, drug-containing granules can be mixed with desired excipients and the mixture can be compressed into tablets or filled into capsules.

Solid pharmaceutical dosage units contain one or more drug substances, together with any desired number of excipients, such as, but not limited to, one or more of diluents, binders, drug stabilizers, disintegrants, glidants, lubricants, release rate modifiers, preservatives, antioxidants, coatings, colorants, flavoring agents, etc.

Various useful fillers or diluents according to the present application include, but are not limited to, starches, cellulose derivatives, sugars, and the like. Various grades of lactose include, but are not limited to, lactose monohydrate, lactose DT, lactose anhydrous, and others. Different starches include, but are not limited to, maize starch, potato starch, rice starch, wheat starch, pregelatinized starch, and others. Different cellulose compounds that can be used include crystalline cellulose and powdered cellulose. Other useful diluents include, but are not limited to, carmellose, sugar alcohols such as mannitol, sorbitol, and xylitol, calcium carbonate, magnesium carbonate, dibasic calcium phosphate, and tribasic calcium phosphate.

Various useful binders according to the present application include, but are not limited to, hydroxypropyl celluloses in various grades, hydroxypropyl methylcelluloses (e.g., Methocel™ products) and useful in various grades, polyvinylpyrrolidones (such as grades K25, K29, K30, and K90), copovidones (e.g., Plasdone™ S 630), powdered acacia, gelatin, guar gum, carbomers (e.g., Carbopol™ products), methylcelluloses, polymethacrylates, and starches. A binder may optionally be included in a granulating fluid.

Modification of drug release into fluids of the gastrointestinal tract sometimes is desirable. For example, a very soluble drug that is rapidly metabolized by the body can desirably be released from a pharmaceutical dosage form over a period of hours, following oral administration. This can be accomplished by including polymeric substances in the body of a tablet. Suitable polymeric substances for this purpose include the "binder" materials described above, as well as polymers described below as being useful for forming coatings.

Various useful disintegrants include, but are not limited to, carmellose calcium, carboxymethylstarch sodium, croscarmellose sodium, crospovidones, examples of commercially available crospovidone products including but not limited to crosslinked povidones, Kollidon™ CL from BASF (Germany), Polyplasdone™ XL, XI-10, and INF-10 from ISP Inc. (USA), and low-substituted hydroxypropyl celluloses. Examples of low-substituted hydroxypropyl celluloses include, but are not limited to, low-substituted hydroxypropylcellulose LH11, LH21, LH31, LH22, LH32, LH2O, LH30, LH32 and LH33 (all supplied by Shin-Etsu Chemical Co., Ltd.). Some other useful disintegrants include sodium starch glycolate, colloidal silicon dioxide, and various starches.

In embodiments, formulations of the present application contain at least one antioxidant, for enhancing the stability of a drug. The antioxidant may be present either as a part of the composition or a packaging component. The antioxidant is present in amounts effective to retard decomposition of the drug that is susceptible to oxidation. In embodiments, the content of an antioxidant in the formulations ranges from about 0.001 to 10 weight percent, with respect to the active agent content. Non-limiting examples of antioxidants include one or more of ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate. Other suitable antioxidants will be readily recognized by those skilled in the art.

Useful lubricants include magnesium stearate, glyceryl monostearate, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof.

One or more glidant materials, which improve the flow of powder blends, pellets, etc. and help to minimize dosage form weight variations, can be used. Useful glidants include, but are not limited to, silicon dioxide, talc, kaolin, and any combinations thereof.

Coloring agents can be used to color code compositions, for example, to indicate the type and dosage of the therapeutic agent therein. Suitable coloring agents include, without limitation, natural and/or artificial compounds such as FD&C coloring agents, natural juice concentrates, pigments such as titanium oxide, silicon dioxide, iron oxides, zinc oxide, any combinations of two or more thereof, and the like.

Solid pharmaceutical dosage forms may be provided with outer coatings that modify the release characteristics of the contained drug or drugs, after administration. Other types of coatings are merely esthetic, or serve to protect the dosage forms against physical damage, moisture ingress, etc. during packaging, shipping, and use. The coatings typically comprise at least one pH-independent or pH-dependent polymer as the major ingredient, frequently also including any one or more of various additives.

Suitable pH-independent polymers that are considered to be water-soluble include both solution formers and polymeric substances that do not form true solutions, but swell upon contact with water to form colloidal dispersions having the appearance of solutions. Representative members include, but are not limited to: polyvinyl alcohols; cellulose ethers, such as methylcelluloses having nominal viscosities in the range of about 3 to about 5000 mPa·s, hydroxyethyl celluloses having nominal viscosities in the range of about 3 to about 5000 mPa·s, hydroxyethylmethyl celluloses having nominal viscosities in the range of about 100 to 70000 mPa·s, hydroxypropyl celluloses ("HPC") having nominal viscosities in the range of about 10 to about 5000 mPa·s, and hydroxypropyl methylcelluloses (hypromelloses or "HPMC"), of various grades such as "E", "F", and "K," having nominal viscosities in the range of about 1 to about 20000 mPa·s; polyvinylpyrrolidones (povidones or "PVP") having nominal molecular weights in the range of about 4000 to about 1,300,000; copovidone; macrogols having molecular weights in the range of about 400 to about 8000; graft copolymers of polyvinyl alcohols and macrogols; polyvinyl caprolactam-polyvinyl acetate-polyethylene glycol graft copolymers; and polymethacrylates. The viscosities are usually measured using a 2% by weight aqueous solution, at 20° C.

Water-insoluble pH-independent polymers include substances such as methylcelluloses, ethylcelluloses, cellulose acetates, and others. As is known in the art, some polymers have an aqueous solubility that depends on their molecular weights.

Various pH-dependent polymers for use in the present application include, but are not limited to, polymers and copolymers of acrylic and methacrylic acids, cellulose acetate butyrates, cellulose acetate phthalates, hydroxypropyl methylcellulose phthalates and succinates, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), and any mixtures of two or more thereof.

Useful additives for coatings include, but are not limited to, plasticizers, antiadherents, opacifiers, solvents, and optionally colorants, lubricants, pigments, antifoam agents, and polishing agents.

Various useful plasticizers include, but are not limited to, substances such as castor oil, diacetylated monoglycerides, dibutyl sebacate, diethyl phthalate, glycerin, polyethylene glycol, propylene glycol, triacetin, and triethyl citrate, and mixtures thereof. The type of plasticizer depends upon the type of coating agent. An opacifier such as titanium dioxide may also be present in amounts ranging from about 0.5-20%, based on the total weight of the coating.

Anti-adhesives are frequently used in film coating processes to avoid sticking effects during film formation and drying. An example of a useful anti-adhesive for this purpose is talc. An anti-adhesive is frequently present in the film coating in amounts about 0.5-15%, based upon the total weight of the coating.

Various solvents that can be used in processes of preparing pharmaceutical formulations of the present application include, but are not limited to, water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N-dimethylformamide, tetrahydrofuran, and any mixtures of two or more thereof.

The foregoing lists of excipient substances are not exhaustive, but are representative of members of the various categories. Those skilled in the art will be aware of many other useful substances, and their use is specifically contemplated herein. Also, it is well-known that many excipients can serve more than one purpose in pharmaceutical formulations. Co-processed excipients, such as combinations of lactose and starch, microcrystalline cellulose and colloidal silica, etc. can sometimes have advantages over using the individual components.

Particle sizes of powders and suspended powders may be determined using any of conventional technologies, including sieve sizing, optical microscopy, Coulter Counter™ electrical zone sensing methods, laser light diffraction (such as with equipment sold by Malvern Instruments Ltd. and Horiba Instruments, Inc.), etc. Particle size distributions frequently are represented by terms such as $D_{10}$, $D_{50}$, $D_{90}$, and the like, where the numerical portion is the percentage of measured particles having a dimension that does not exceed the given size. For example, $D_{90}=10$ μm means that 90 percent of the particles have sizes that do not exceed 10 μm in any dimension. Suspended particle sizes optionally can be measured using various physiological media to form the suspensions, e.g., simulated gastric fluid (pH 1.2), acetate buffer (pH 4.5) and simulated intestinal fluid (pH 5.5-7.5), or using water or a buffered or unbuffered aqueous medium.

Pharmaceutical products can be tested for their drug dissolution characteristics, such as using test 711 "Dissolution" in *United States Pharmacopeia* 24, United States Pharmacopeial Convention, Inc., Rockville, Md., 1999 ("USP"). Various fluids can be used as the dissolution media, including acids, buffers, simulated digestive tract fluids, etc., and many of these are defined in various monographs of the USP. An example of a procedure uses "Apparatus 2," which has a vessel containing a medium that is stirred with a rotating paddle. Typically, a dosage unit is immersed into the medium and samples of the medium are withdrawn at intervals for drug content analysis, frequently using HPLC techniques.

An example of a HPLC method for analyzing fesoterodine fumarate and its degradants was described by B. V. R. Reddy et al., "A Validated Stability-Indicating HPLC Assay Method for Determination of Fesoterodine Fumarate," *RASĀYAN Journal of Chemistry*, Vol. 5(2), pages 239-245, 2012.

The following examples describe certain specific aspects and embodiments in greater detail, are provided solely for purposes of illustration, and should not be construed as limiting the scope of the disclosure in any manner.

EXAMPLE 1

The effects of excipient substances on the stability of fesoterodine hydrogen fumarate are studied by mixing powders of the drug and excipients, then storing samples of the mixtures open to the atmosphere at 40° C. and 75% relative humidity, for 2 days or 5 days. Xylitol alone and maltitol alone are used as comparator excipients. The amounts of drug-related degradant impurities are determined in the prepared mixtures and stored samples, using a HPLC procedure. Results are shown in the following table, where amounts of drug degradants are expressed as percentages of the initial drug concentration. In the table, "DF" is deacyl fesoterodine and drug:excipient proportions are by weight.

|  | Degradant Content | | | | | |
|---|---|---|---|---|---|---|
|  | DF | | | Total | | |
| Mixture | Initial | 2 Days | 5 Days | Initial | 2 Days | 5 Days |
| Drug + xylitol (1:2) | 0.116 | 0.126 | 0.137 | 0.324 | 0.321 | 0.370 |
| Drug + xylitol (1:6) | 0.102 | 0.128 | 0.119 | 0.283 | 0.309 | 0.406 |
| Drug + xylitol (1:9) | 0.108 | 0.139 | 0.136 | 0.314 | 0.406 | 0.403 |
| Drug + fructose (1:9) | 0.104 | 0.384 | — | 0.365 | 0.866 | — |
| Drug + maltitol (1:3) | 0.110 | 0.335 | 0.478 | 0.383 | 0.540 | 0.816 |
| Drug + maltitol (1:6) | 0.112 | 0.358 | 0.515 | 0.315 | 0.582 | 0.868 |
| Drug + maltitol (1:9) | 0.116 | 0.433 | 0.549 | 0.310 | 0.625 | 0.893 |
| Drug + maltitol (1:12) | 0.108 | 0.586 | 0.796 | 0.297 | 0.831 | 1.236 |
| Drug + xylitol + maltitol (1:2:2) | 0.108 | 0.120 | 0.124 | 0.320 | 0.295 | 0.329 |
| Drug + xylitol + maltitol (1:2:4) | 0.111 | 0.132 | 0.131 | 0.345 | 0.335 | 0.339 |
| Drug + xylitol + maltitol (1:2:7) | 0.120 | 0.127 | 0.128 | 0.396 | 0.303 | 0.372 |

EXAMPLE 2

An extended release tablet formulation is prepared, using the ingredients in the table below.

| Ingredient | mg/Tablet |
|---|---|
| Fesoterodine fumarate | 8 |
| Fructose, granular | 72 |
| Water* | 2 |
| StarLac ®† | 77.5 |
| Hypromellose (Methocel ® K100M Premium) | 120 |
| Hypromellose (Methocel K4M Premium) | 24 |
| Talc (500 grade) | 8.5 |
| Glyceryl behenate (COMPRITOL ® 888 ATO) | 10 |
| Coating | |
| OPADRY ® AMB 80W105004 (dark blue)** | 15 |
| Water* | 60 |

†A spray-dried composition containing 85% α-lactose monohydrate and 15% maize starch, from Meggle Group.
*Evaporates during processing, not present in the final product.
**OPADRY AMB products, from Colorcon, are formulated moisture barrier coating compositions containing a polyvinyl alcohol polymer.

Formulation Process:
1. Fesoterodine fumarate and fructose are blended, then granulated by spraying with water. The granules are dried and milled to an average particle size not exceeding 1200 μm.
2. StarLac and the hypromellose ingredients are blended, then mixed with the granules. Talc and glyceryl behenate are sequentially added with blending.
3. The mixture is compressed into tablets, coated with the coating suspension, and dried.

Tablets prepared as above and commercial TOVIAZ fesoterodine tablets, 8 mg are tested for their drug dissolution characteristics using the USP dissolution method in apparatus 2 (paddle) with 900 mL of phosphate buffer (pH 6.8) and 75 rpm stirring. The results are shown in the following table, wherein the numeric values are cumulative percentages of the label drug content that dissolve.

| Time (hours) | TOVIAZ (Lot No. V111327) | Example 2 |
|---|---|---|
| 0 | 0 | 0 |
| 1 | 14 | 11 |
| 2 | 24 | 22 |
| 4 | 40 | 41 |
| 6 | 52 | 56 |
| 8 | 62 | 69 |
| 12 | 76 | 83 |
| 16 | 85 | 93 |
| 20 | 89 | 98 |

Prepared tablets are analyzed for their drug degradant impurities, both as prepared and following four weeks of storage, open to the atmosphere at 40° C. and 75% relative humidity. Results obtained using a HPLC procedure are shown in the table below, where numeric values are percentages of the label drug content.

| Impurity | Initial | Stored |
|---|---|---|
| Deacyl fesoterodine | 0.053 | 0.146 |
| Total | 0.305 | 0.461 |

EXAMPLE 3

An extended release tablet formulation is prepared, using the ingredients in the table below.

| Ingredient | mg/Tablet |
|---|---|
| Fesoterodine fumarate | 8 |
| Xylitol | 16 |
| Maltitol | 32 |
| Water* | 1.5 |
| StarLac | 95.5 |
| Hypromellose (Methocel K100M Premium) | 120 |
| Hypromellose (Methocel K4M Premium) | 24 |
| Talc (500 grade) | 8.5 |
| Glyceryl behenate (COMPRITOL 888 ATO) | 10 |
| Coating | |
| Opadry AMB 80W105004 (dark blue) | 15 |
| Water* | 60 |

*Evaporates during processing, not present in the final product.

The formulation process is similar to that described in Example 2, except that a mixture of maltitol and xylitol is used for granulation with the drug, instead of fructose.

Tablets prepared as above and commercial TOVIAZ fesoterodine tablets, 8 mg are tested for their drug dissolution characteristics using the USP dissolution method in apparatus 2 (paddle) with 900 mL of phosphate buffer (pH 6.8) and 75 rpm stirring. The results are shown in the following table, wherein the numeric values are cumulative percentages of the label drug content that dissolve.

| Time (hours) | TOVIAZ (Lot No. V111327) | Example 3 |
|---|---|---|
| 0 | 0 | 0 |
| 1 | 14 | 14 |
| 2 | 24 | 24 |
| 4 | 40 | 40 |
| 6 | 52 | 52 |
| 8 | 62 | 62 |
| 12 | 76 | 76 |
| 16 | 85 | 84 |
| 20 | 89 | 89 |

Prepared tablets are analyzed for their drug degradant impurities, both as prepared and following four weeks of storage, open to the atmosphere at 40° C. and 75% relative humidity. Results obtained using a HPLC procedure are shown in the table below, where numeric values are percentages of the label drug content.

| Impurity | Initial | Stored |
|---|---|---|
| Deacyl fesoterodine | 0.052 | 0.200 |
| Total | 0.288 | 0.492 |

EXAMPLE 4

Tablets containing 4 mg (Formulation A) or 8 mg (Formulation B) of fesoterodine fumarate are prepared using the ingredients in the following table.

| | Kilograms | |
|---|---|---|
| Ingredient | Formulation A | Formulation B |
| Fesoterodine fumarate | 0.5 | 1 |
| Fructose, granular | 9 | 9 |
| Water* | 0.25 | 0.25 |
| StarLac | 10.187 | 9.687 |
| Hypromellose (Methocel K100M Premium) | 15 | 15 |
| Hypromellose (Methocel K4M Premium) | 3 | 3 |
| Talc (500 grade) | 1.063 | 1.063 |
| Glyceryl behenate (COMPRITOL 888 ATO) | 1.25 | 1.25 |
| Coating | | |
| OPADRY AMB 80W99006 (light blue) | 1.875 | — |
| OPADRY AMB 80W105004 (dark blue) | — | 1.875 |
| Water* | 7.5 | 7.5 |

*Evaporates during processing, not present in the final product.

Formulation Process:

1. Milled fesoterodine fumarate ($D_{90} \leq 10$ µm) and fructose are passed through a 20 mesh sieve and blended in a high shear mixer, then water is sprayed onto the mixture. The formed granules are briefly kneaded, then dried at about 45° C. until the loss on drying at 65° C. is 0.5% or less. Granules are passed through a comminuting mill having a screen with 1.02 mm round holes and 30% open area.

2. StarLac and the hypromellose ingredients are passed through a 20 mesh sieve and blended with the granules, then talc (passing through a 30 mesh sieve) is added and blended. Glyceryl behenate is passed through a 30 mesh sieve, added to the blender, and blending is continued to achieve uniformity.

3. The blend is compressed to form tablets weighing 320 mg and having a hardness about 10 kiloponds.

4. The coating suspension is sprayed onto tablets in a coating pan, and the coated tablets are dried.

Further specific aspects and embodiments are described in the following paragraphs A-F.

A. A pharmaceutical formulation comprising a co-granulate containing a moisture-sensitive drug and fructose.

B. The pharmaceutical formulation of paragraph A, wherein a weight ratio of drug to fructose is about 1:9.

C. A pharmaceutical formulation comprising a co-granulate containing a moisture-sensitive drug, xylitol, and maltitol.

D. The pharmaceutical formulation of paragraph C, wherein a weight ratio of drug to xylitol to maltitol is about 1:2:4.

E. The pharmaceutical formulation listed in any of paragraphs A-D, wherein a drug is fesoterodine fumarate.

F. Tablets prepared according to the procedure described in any of Examples 2-4.

What is claimed is:

1. A pharmaceutical formulation comprising a co-granulate comprising a moisture-sensitive drug and an excipient comprising a mixture of xylitol and maltitol, wherein the moisture-sensitive drug, xylitol, and maltitol are present in a weight ratio in the range of about 1:2:2 to 1:2:7.

2. The pharmaceutical formulation of claim 1, wherein the moisture-sensitive drug, xylitol, and maltitol are present in a weight ratio of about 1:2:4.

3. The pharmaceutical formulation of claim 1, wherein the moisture-sensitive drug comprises fesoterodine fumarate.

4. The pharmaceutical formulation of claim 1, further comprising a diluent, a binder, a drug stabilizer, a disintegrant, a glidant, a lubricant, a release rate modifier, a preservative, an antioxidant, a coating, a colorant, a flavoring agent, or combinations thereof.

5. A method of producing a pharmaceutical tablet, the method comprising:
forming a blend of a moisture-sensitive drug and a first excipient comprising a mixture of xylitol and maltitol, and combinations thereof, wherein the moisture-sensitive drug, xylitol, and maltitol are present in a weight ratio in the range of about 1:2:2 to 1:2:7;
spraying the blend with water to produce granules;
drying and milling the granules;
mixing a second excipient with the granules; and
compressing into tablets.

6. The method of claim 5, wherein the second excipient is selected from the group consisting of diluent, binder, drug stabilizer, disintegrant, glidant, lubricant, release rate modifier, preservative, antioxidant, coating, colorant, flavoring agent, and combinations thereof.

7. The method of claim 5, wherein the moisture-sensitive drug comprises fesoterodine fumarate.

8. The method of claim 5, wherein the granules are dried and milled to an average particle size of less than 1200 µm.

9. The method of claim 5, further comprising coating the tablets with a coating suspension.

10. The pharmaceutical formulation of claim 1, wherein the moisture-sensitive drug comprises a drug compound that is susceptible to degradation by formation of one or more impurities.

11. The pharmaceutical formulation of claim 1, wherein moisture-sensitive drug comprises a drug compound that is susceptible to degradation by deacylation and formation of an impurity comprising a deacylated drug compound.

* * * * *